United States Patent
Lu et al.

(10) Patent No.: US 10,638,920 B2
(45) Date of Patent: May 5, 2020

(54) METHOD AND APPARATUS OF LENS ALIGNMENT FOR CAPSULE

(71) Applicant: CapsoVision, Inc., Saratoga, CA (US)

(72) Inventors: Ganyu Lu, Palo Alto, CA (US); Gordon C. Wilson, San Francisco, CA (US); Kang-Huai Wang, Saratoga, CA (US)

(73) Assignee: CAPSOVISION INC, Saratoga, CA (US)

( * ) Notice: Subject to any disclaimer, the term of this patent is extended or adjusted under 35 U.S.C. 154(b) by 29 days.

(21) Appl. No.: 16/092,301

(22) PCT Filed: Jun. 1, 2017

(86) PCT No.: PCT/US2017/035553
§ 371 (c)(1),
(2) Date: Oct. 9, 2018

(87) PCT Pub. No.: WO2017/218206
PCT Pub. Date: Dec. 21, 2017

(65) Prior Publication Data
US 2019/0150717 A1    May 23, 2019

Related U.S. Application Data

(60) Provisional application No. 62/349,602, filed on Jun. 13, 2016.

(51) Int. Cl.
*A61B 1/04* (2006.01)
*H04N 5/225* (2006.01)
(Continued)

(52) U.S. Cl.
CPC ............ *A61B 1/041* (2013.01); *A61B 5/0031* (2013.01); *G02B 13/06* (2013.01); *G02B 13/16* (2013.01);
(Continued)

(58) Field of Classification Search
CPC ....... A61B 1/041; H04N 5/2254; G02B 13/06
See application file for complete search history.

(56) References Cited

U.S. PATENT DOCUMENTS 9,638,883 B1 *  5/2017  Duparre ................. G02B 7/003
2002/0109774 A1 *  8/2002  Meron ............... A61B 1/00096
348/74

(Continued)

OTHER PUBLICATIONS

"Optics" by Eugene Hecht ("Optics"—5th Edition, Published by Pearson Education, Inc., 2017, Section 5.2, p. 171-173, ISBN 13: 978-0-133-97722-6).

*Primary Examiner* — Robert J Hance
(74) *Attorney, Agent, or Firm* — Blairtech Solution LLC

(57) ABSTRACT

A method and apparatus of aligning a lens module with respect to an image sensor device for a capsule camera are disclosed. The image sensor device comprises multiple pixel arrays and the lens module comprises multiple lens sets to form multiple images corresponding to multiple fields of view associated with the multiple lens sets, and each lens set forms one image for one corresponding pixel array associated with one field of view. A method according to the present invention present invention, one or more test images are presented in the multiple fields of view associated with the lens module. Multiple images in the multiple fields of view are captured using the multiple pixel arrays. Metric measurement is derived based on the multiple images captured by the multiple pixel arrays. Lens alignment between the lens module and the image sensor device is then adjusted based on the metric measurement.

16 Claims, 8 Drawing Sheets

(51) Int. Cl.
*H04N 5/232* (2006.01)
*H04N 5/228* (2006.01)
*G02B 13/16* (2006.01)
*G03B 37/02* (2006.01)
*G03B 37/04* (2006.01)
*G03B 37/00* (2006.01)
*A61B 5/00* (2006.01)
*G02B 13/06* (2006.01)
*H04N 5/341* (2011.01)

(52) U.S. Cl.
CPC ........... *G03B 37/005* (2013.01); *G03B 37/02* (2013.01); *G03B 37/04* (2013.01); *H04N 5/228* (2013.01); *H04N 5/2254* (2013.01); *H04N 5/23238* (2013.01); *H04N 5/3415* (2013.01); *G03B 2215/0503* (2013.01); *H04N 2005/2255* (2013.01)

(56) References Cited

U.S. PATENT DOCUMENTS

| | | |
|---|---|---|
| 2006/0170886 A1 | 8/2006 | Kitabayashi |
| 2006/0216014 A1* | 9/2006 | Morinaga ............. G02B 7/026 396/144 |
| 2007/0285553 A1 | 12/2007 | Morita |
| 2008/0166072 A1 | 7/2008 | Wang |
| 2009/0135245 A1 | 5/2009 | Luo |
| 2011/0001789 A1* | 1/2011 | Wilson .................. G02B 13/06 348/36 |
| 2013/0088637 A1* | 4/2013 | Duparre .............. H04N 5/2254 348/360 |
| 2014/0002674 A1* | 1/2014 | Duparre ................ G02B 7/003 348/187 |
| 2016/0014405 A1* | 1/2016 | Beckman ............ H04N 17/002 348/187 |

* cited by examiner

METHOD AND APPARATUS OF LENS ALIGNMENT FOR CAPSULE

CROSS REFERENCE TO RELATED APPLICATIONS

The present invention claims priority to U.S. Provisional Application Ser. No. 62/349,602, filed on Jun. 13, 2016. The present invention is related to U.S. Patent Application The present invention is related to U.S. patent application, Ser. No. 14/660,365, filed on Mar. 17, 2015, which is a continuation of U.S. patent application, Ser. No. 12/877,220, filed on Sep. 8, 2010, now U.S. Pat. No. 9,001,187 issued on Apr. 7, 2015, which is a continuation-in-part of U.S. patent application, Ser. No. 12/463,488, filed on May 11, 2009, now U.S. Pat. No. 8,717,413 issued on May 6, 2014, which is a non-Provisional U.S. Patent Application of Provisional Application No. 61/052,180, filed on May 10, 2008. The present invention is also related to U.S. Pat. No. 7,817,354, issued on Oct. 19, 2010 and U.S. Pat. No. 9,118,850, issued on Aug. 25, 2015. The U.S. Non-Provisional Patent Applications and U.S. Provisional Applications are hereby incorporated by reference in their entireties.

FIELD OF THE INVENTION

The present invention relates to capsule camera having a lens module and multiple image sensor arrays, where the lens module comprises multiple lens sets. In particular, the present invention relates to techniques to perform alignment between the lens module and the multiple image sensor arrays.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

U.S. Pat. Nos. 6,709,387 and 6,428,469 describe details of such a system. An autonomous capsule camera system with on-board data storage was disclosed in the U.S. Pat. No. 7,983,458, issued on Jul. 19, 2011.

An optical imaging system and method for producing panoramic images exhibiting a substantial field of view for capsule camera applications are disclosed in U.S. Pat. No. 7,817,354, issued on Oct. 19, 2010. In one embodiment, this optical imaging system comprises a four-sided reflective pyramid and four folded centers of perspective at which entrance pupils of individual image sensor array may be positioned. Each of the image sensor arrays so positioned has an optical axis associated therewith that is folded by the reflective facets of the pyramid. Each individual image sensor array positioned at a respective folded center of perspective each has a horizontal field-of-view (HFOV) of at least 90.degree. Therefore, a composite HFOV constructed from the combined individual fields-of-view is 360°.

FIG. 1 illustrates an example of a swallowable capsule system 100 according to an embodiment as disclosed in U.S. Pat. No. 7,817,354. Capsule system 100 is entirely autonomous while inside the body, with all of its elements encapsulated in a capsule housing 110 that provides a moisture barrier, protecting the internal components from bodily fluids. Capsule housing 110 is transparent, so as to allow light from the light-emitting diodes (LEDs) of illuminating system 12 to pass through the wall of capsule housing 110 to the lumen walls, and to allow the scattered light from the lumen walls to be collected and imaged within the capsule. Capsule housing 110 also protects lumen from direct contact with the foreign material inside capsule housing 110. Capsule housing 110 is provided a shape that enables it to be swallowed easily and later to pass through of the GI tract. Generally, capsule housing 110 is sterile, made of non-toxic material, and is sufficiently smooth to minimize the chance of lodging within the lumen.

As shown in FIG. 1, capsule system 100 includes illuminating system 120 and a camera that includes optical system (140A and 140B) and image sensor 160. The optical system comprises multiple lens sets. While only two lens sets (140A and 140B) are shown in FIG. 1, more lens sets (e.g. 4) may be used. The image sensor 160 comprises multiple sensor arrays to match the number of lens sets in order to capture the images projected by the multiple lens sets. An image captured by image sensor 160 may be processed by process sub-system and battery 180, which provides all the needed processing and controls (e.g., image processing, compression, storage, etc.).

Illuminating system 12 may be implemented by LEDs. In FIG. 1, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

The optical imaging system disclosed in U.S. Pat. No. 7,817,354 is capable of providing a combined individual fields-of-view of 360°. In U.S. Pat. Nos. 9,001,187 and 8,717,413, another optical system is disclosed that is also capable of providing a combined individual fields-of-view of 360°, that discloses lenses of negative refractive power positioned before the first surface of each prism. FIG. 2 illustrates a perspective view of a partially assembled panoramic camera system employing four folded imagers according to U.S. Pat. No. 8,717,413. In particular, shown positioned within lens module housing 210 are spindle 220, four prisms 250, four lens elements 240 of negative refractive power. Shown in this figure are notches 255 formed on a front face of each prism 250, and mating tabs 845 formed on back (prism side) of each lens 245. Such notches and tabs provide a secure, positive alignment between the lenses 240 and the prisms 250.

In U.S. Pat. No. 9,118,850, a camera system with multiple pixel arrays on a chip is disclosed. FIG. 3 shows an exemplary layout 300 for an integrated sensing component with multiple pixel arrays according to the present invention to support the four images corresponding to the four optical paths. The multiple pixel arrays and associated timing/control circuits and common readout chain are implemented on a common substrate 350, such as a semiconductor material. The integrated multiple pixel-array image sensing component comprises separate pixel arrays 311, 312, 313 and 314. The pixel arrays are configured so that each pixel array is located and oriented properly to capture a corresponding image formed by a lens sub-system. Besides pixel arrays 311, 312, 313 and 314, other components may also be formed on substrate 350. For example, timing and control block 320, one or more readout chains (e.g., read out chain 330) for reading out electrical output signals from the pixel arrays, and I/O ring structures 340 can also be formed on the same substrate 350. The readout chain 330 processes the output signals from the pixel arrays before sending out the electrical signal through I/O ring structure 340. In FIG. 3, the center of the four sensor arrays is indicated by a black dot 360.

When coupled with a matched optical system, the multiple pixel arrays can capture scenes in a very wide field of view or even a 360° panoramic view. The camera system uses one or more image sensor IC chips each having multiple pixel arrays on the same semiconductor substrate (i.e., "multiple pixel arrays on a chip"). Additional electronic components for further signal processing of the captured images are also disclosed.

In a conventional camera system with a single lens set, the single lens set and the sensor(s) has to be aligned in order to optimize the captured image quality. The conventional camera system with a single lens set has only one field of view. The system may use multiple sensors corresponding to multiple color components. In such cases, dichroic beam splitters are often used to direct light from the field of view to individual sensors. For a capsule camera with multiple lens sets coupled to multiple sensor arrays, the alignment between the multiple lens sets and the multiple sensor arrays becomes very critical. With the increasing resolution of the sensor arrays, the alignment becomes even more critical. It is desirable to develop techniques for reliably aligning the multiple lens sets and the multiple sensor arrays.

BRIEF SUMMARY OF THE INVENTION

A method and apparatus of aligning a lens module with respect to an image sensor device for a capsule camera are disclosed. The image sensor device comprises multiple pixel arrays and the lens module comprises multiple lens sets to form multiple images corresponding to multiple fields of view associated with the multiple lens sets, and each lens set forms one image for one corresponding pixel array associated with one field of view. A method according to the present invention present invention, one or more test images are presented in the multiple fields of view associated with the lens module. Multiple images in the multiple fields of view are captured using the multiple pixel arrays. Metric measurement is derived based on the multiple images captured by the multiple pixel arrays. Lens alignment between the lens module and the image sensor device is then adjusted based on the metric measurement.

The lens alignment between the lens module and the image sensor device can be performed in multiple degrees of freedom and second lens alignment in second one or more degrees of freedom is performed after first lens alignment in first one or more degrees of freedom. Adjusting the lens alignment between the lens module and the image sensor device can be performed in the first one or more degrees of freedom and the second lens alignment iteratively until a criterion is met. The criterion may correspond to no further improving image quality by said adjusting the lens alignment.

In one embodiment, the lens module consists of four lens sets arranged laterally to provide a combined individual fields-of-view of 360 degrees and the image sensor device consists of four pixel arrays. The four pixel arrays can be implemented on a common substrate. The test images can be selected from a group comprising "cross hairs", "slant edges", "circles", "dots", "grids", "checker board", "grating lines", and "sinusoidal waves". The metric measurement may correspond to modulation transfer function (MTF), point spread function (PSF), spot size of a pin hole, contrast or maximum achievable spatial resolution.

In one embodiment, the metric measurement is used to determine BFDs (back focus distances) associated with the multiple lens sets and said adjusting the lens alignment is performed according to the BFDs for the multiple lens sets, wherein each back focus distance of one lens set is a distance from an image plane corresponding to a plane of optimal focus to a reference datum in one lens set. In one embodiment, the lens module consists of four lens sets arranged laterally to provide a combined individual fields-of-view of 360 degrees and the image sensor device consists of four pixel arrays, four BFDs designated as Z1, Z2, Z3 and Z4 associated with four neighboring lens sets in a sequential order are determined. In another embodiment, the longitudinal distance between the lens module and the image sensor device is determined according to (Z1+Z2+Z3+Z4)/4. Rotational alignments about x-axis and y-axis are adjusted to minimize (Z2−Z4)/2d and (Z1−Z3)/2d respectively, where d is a lateral distance between two corresponding pixel arrays on two opposite sides. The lens alignment can be adjusted to minimize the alignment error for all quadrants, where the alignment error is determined according to |Z1−Z2+Z3−Z4|/4.

Adjusting the lens alignment may further comprise adjusting translational offset (Tx, Ty) between an optical center of the multiple lens set and a center of the pixel arrays to minimize the translational offset. In one embodiment, the translational offset can be determined using a white cylindrical target as a test image to find a center of each quadrant of the lens module with four lens sets and the center of each quadrant of the lens module is determined from a center of contours of an image of the white cylindrical target. In another embodiment, the image of the white cylindrical target is filtered prior to finding the center of each quadrant of the lens module.

In another embodiment, adjusting the lens alignment may further comprise adjusting rotation value in z-direction, Rz to minimize rotational error. The rotation value can be determined contours of the image of the white cylindrical target. Least square error, a min-max criterion or minimum of largest error in (Tx, Ty) or Rz associated with each quadrant of the lens module can be used as a performance criterion. In yet another embodiment, a target shape, pattern or color is used as a test image to find a center of each quadrant of the lens module with four lens sets and light associated with test image enters a pupil over a field of view of one lens set so that at least a portion of image footprint of the test image is visible on a corresponding pixel array associated with one field of view.

In yet another embodiment, adjusting the lens alignment may further comprise fixing adjustable positions of the lens module after adjusting the lens alignment is completed. The adjustable positions of the lens module are then fixed using UV-cured adhesive.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

As mentioned above, the capsule camera provides a cost effective and painless alternative to the conventional endoscope. The panoramic imaging systems, as disclosed in U.S. Pat. Nos. 9,001,187 and 8,717,413 can produce a composite panoramic image exhibiting a substantial field of view, e.g., 360°. In addition, the system so constructed may advantageously exhibit a substantially larger vertical field of view (VFOV) than prior art systems of comparable size. The lens system forms multiple images corresponding to the multiple fields of view associated with the multiple lens sets with a common optical center. In a capsule camera system, the optical elements for the lens module need to be positioned such that the images are aligned substantially on an image plane. In other words, the lens module has to be aligned with the multiple sensor arrays and one another.

During the manufacturing of a capsule camera system, the components for the capsule camera such as the lens module, sensor arrays, processing circuits, and batteries have to be assembled inside the capsule housing. The image formation and capture path involve the lens module and the sensor arrays. In order to ensure the imaging system to achieve the best possible quality, the lens module and the sensor arrays have to be properly aligned. The present invention discloses a method to align the lens module with the sensor arrays and one another systematically.

Figure 4:
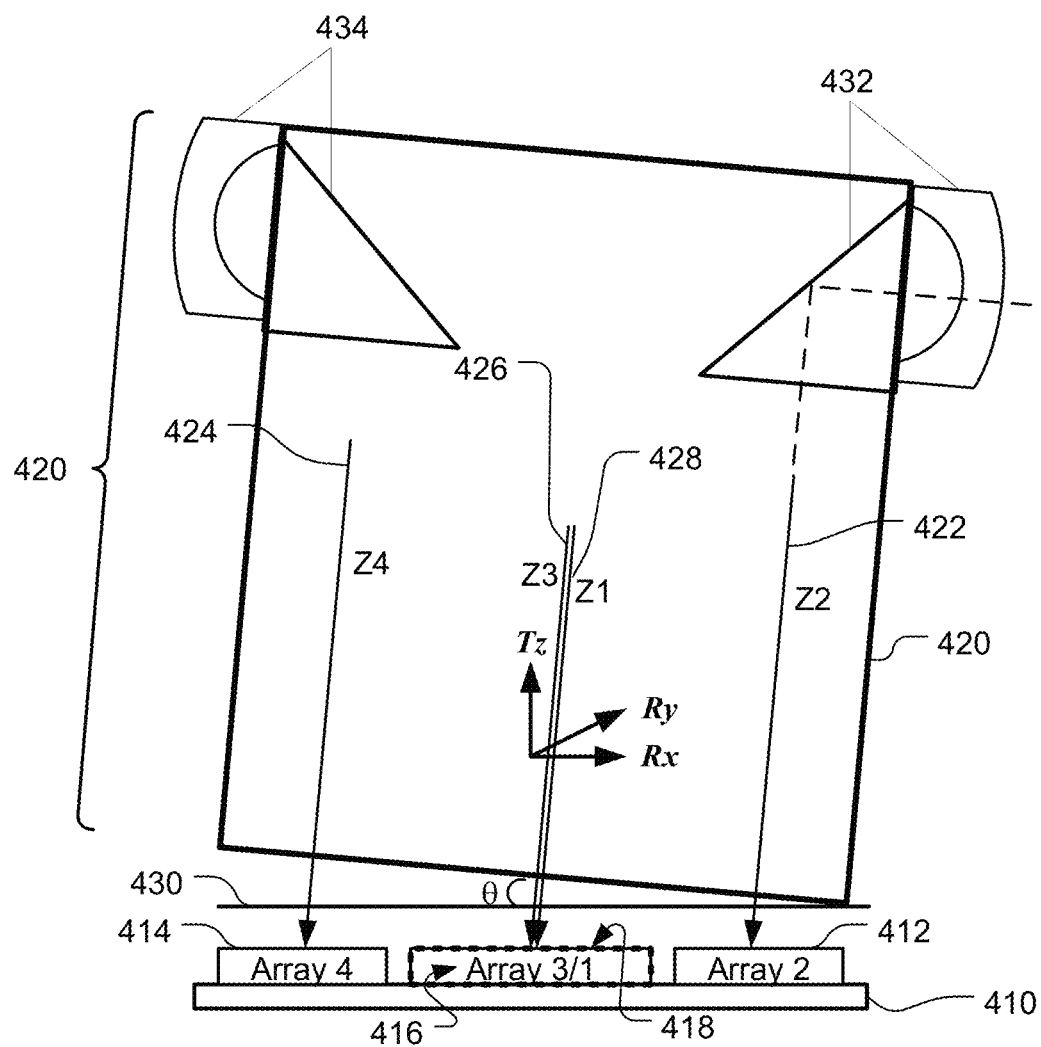
FIG. 4 illustrates an exemplary scenario of misalignment between a lens module and multiple sensor arrays.

FIG. 4 illustrates a cross-section view of a simplified scenario of misalignment between the lens module 420 and the multiple sensor arrays (i.e., array 2 (412), array 4 (414), array 3/1 (416, 418)), where the multiple sensor arrays are fabricated on a common substrate 410. The lens module is shown to be tilted with respect to a plane 430 parallel to the multiple sensor arrays. In particular the lens module is tilted with respect to the plane 430 at an angle θ in the x-direction. The coordinate system is defined with respect to the sensor arrays, where the plane 430 is in parallel with the (x,y)-plane. The z-coordinate is perpendicular to the plane 430. Each lens set of the lens module has a corresponding lens group or groups and a corresponding reflective surface (432, 434) to reflect the incidental light from a corresponding field of view onto a corresponding sensor array (412, 414). For simplicity, the lens sets of the lens module for sensor array 3/1 (416, 418) are not shown. Furthermore, only partial lens groups are shown for the two lens sets shown. The back focus distance (BFD) for each lens set is shown (Z1 428, Z2 422, Z3 426, Z4 424). The BFD of a lens set is the distance from the image plane (plane of optimal focus) to a reference datum in the lens set, such as the last lens surface. In order for the images captured by sensor 410 to be optimally sharp (in focus) for each quadrant, each pixel array should be positioned at the BFD of each lens set. Nominally identical lens sets have equal BFDs, and the lens module should have zero tilt and be adjusted in the z direction to obtain best focus on all pixel arrays. However, in general, manufacturing variability results in unequal BFDs for each lens group (Z1, Z2, Z3, and Z4 are not exactly equal) and the optimal tilt of the lens module may not be zero. In the example of FIG. 4, the optimal alignment of the lens module may be with θ not equal to zero.

Figure 1:
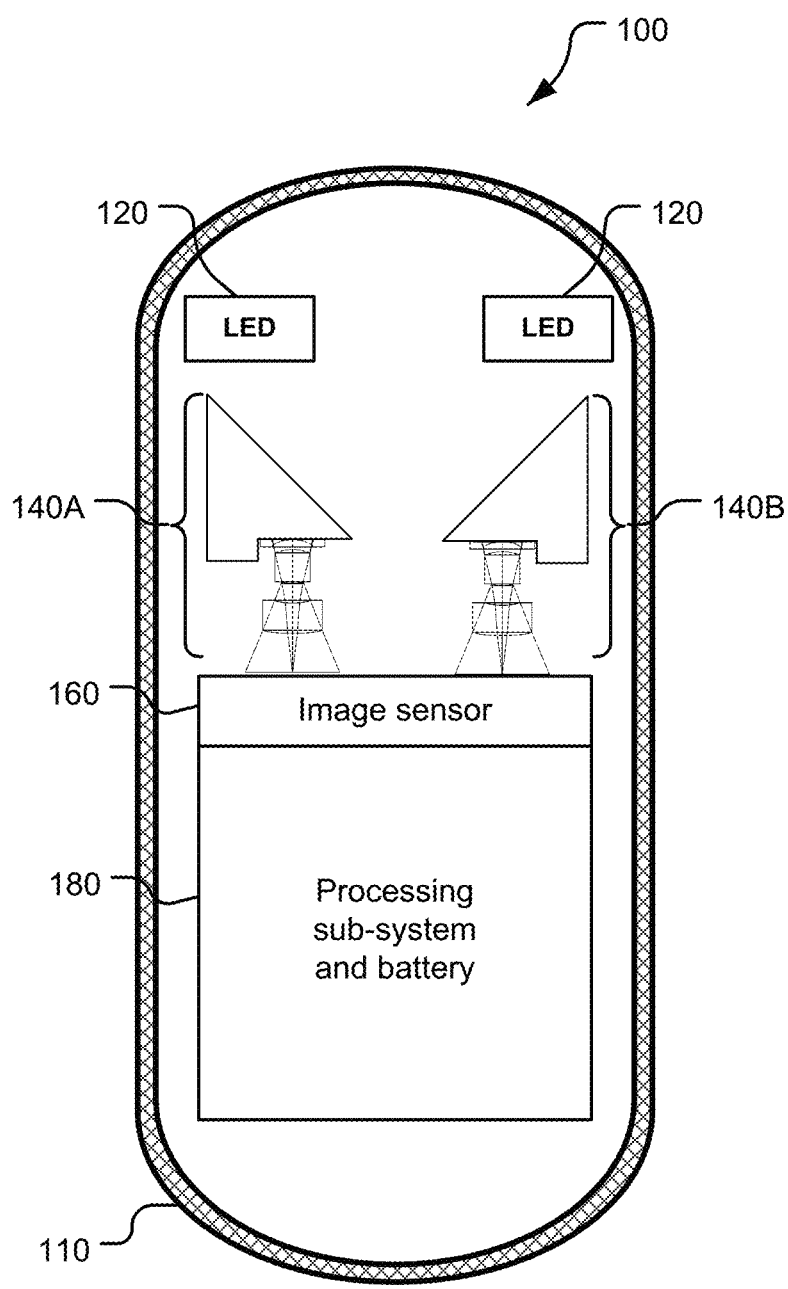
FIG. 1 shows schematically capsule camera system having a lens module with multiple lens sets and corresponding multiple sensor arrays.
Figure 2:
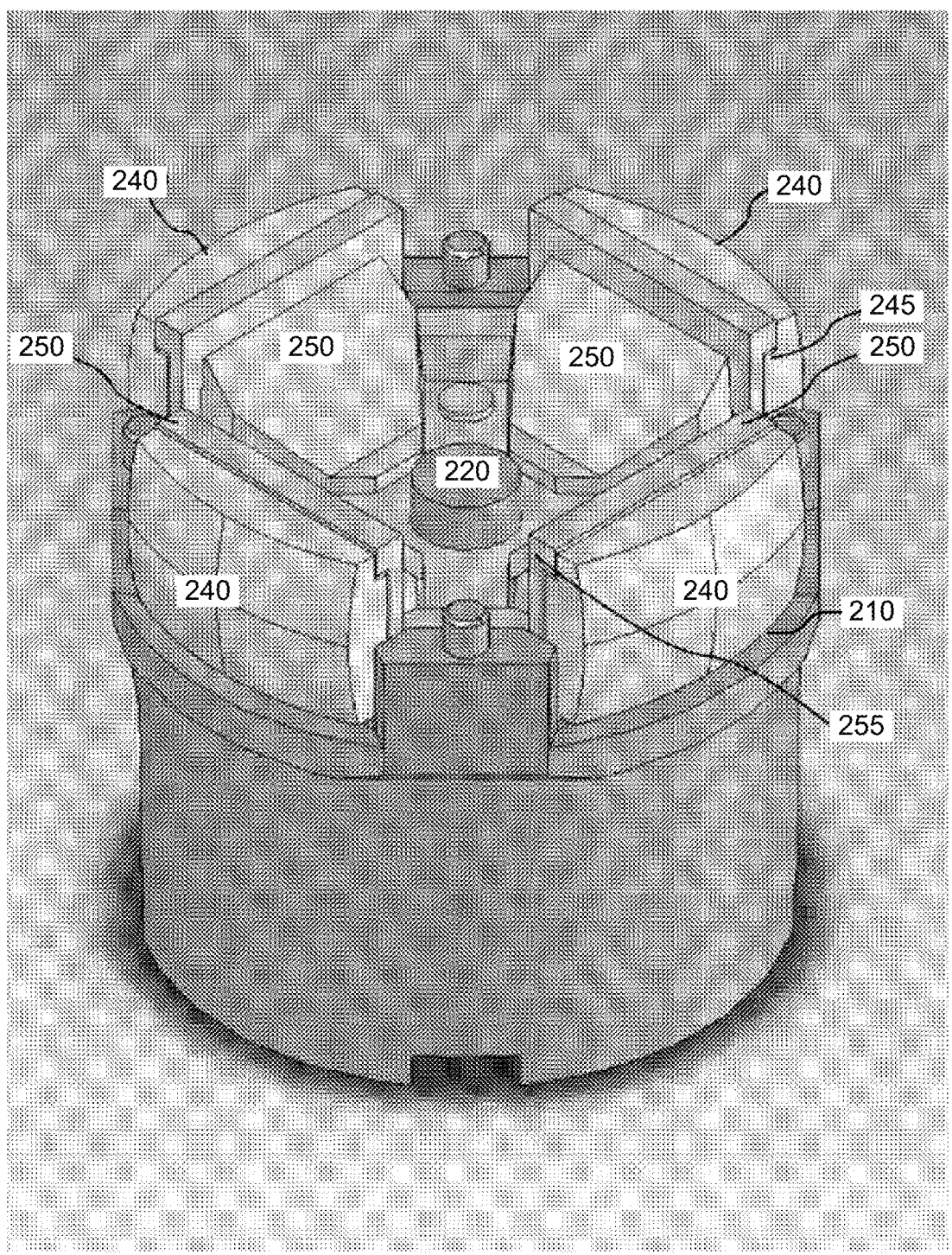
FIG. 2 shows an exemplary lens module having multiple lens sets to provide combined individual fields-of-view 360°.
Figure 3:
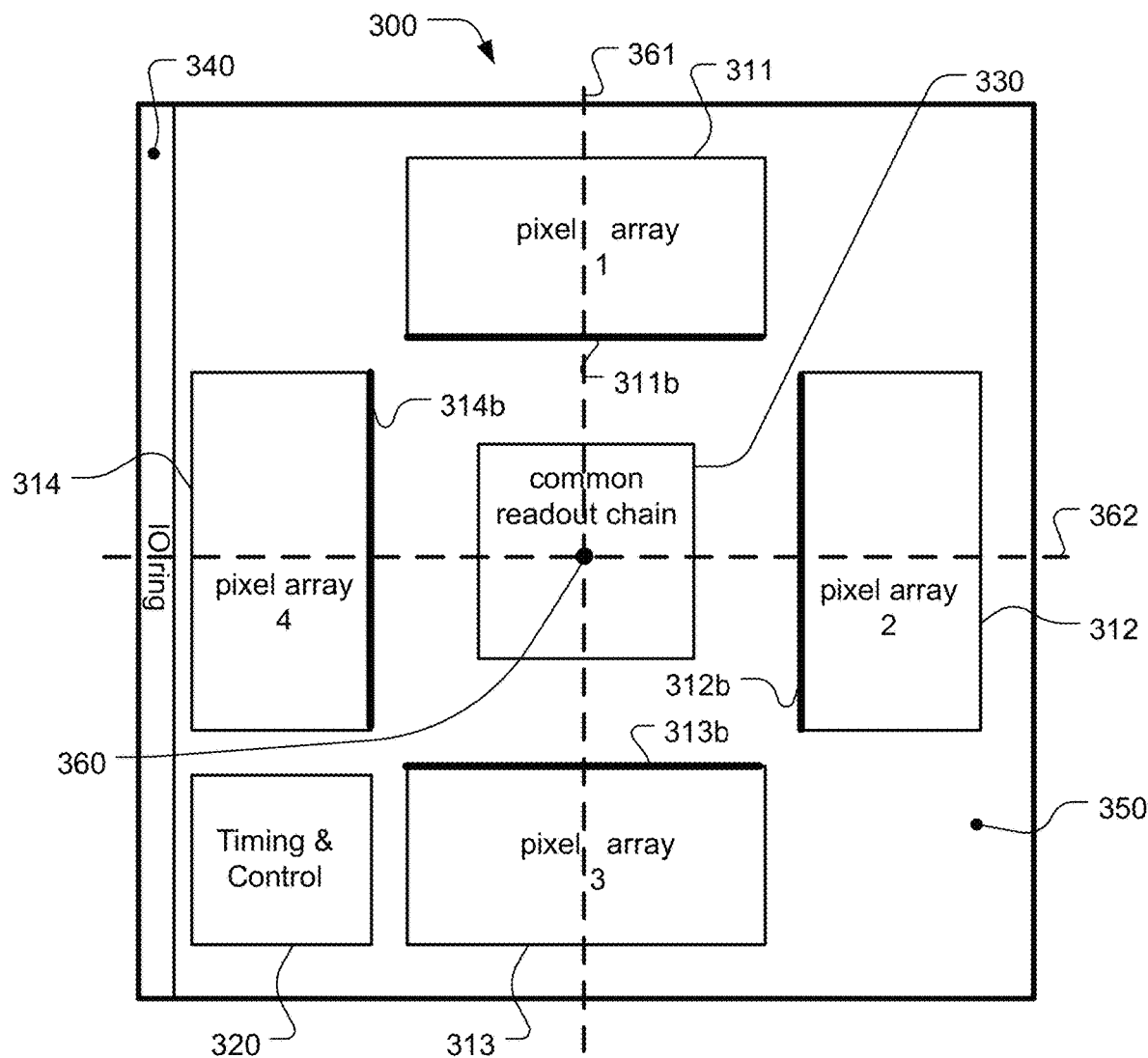
FIG. 3 shows a block diagram for multiple sensor arrays and associated timing and control circuits on a same substrate.
Figure 5:
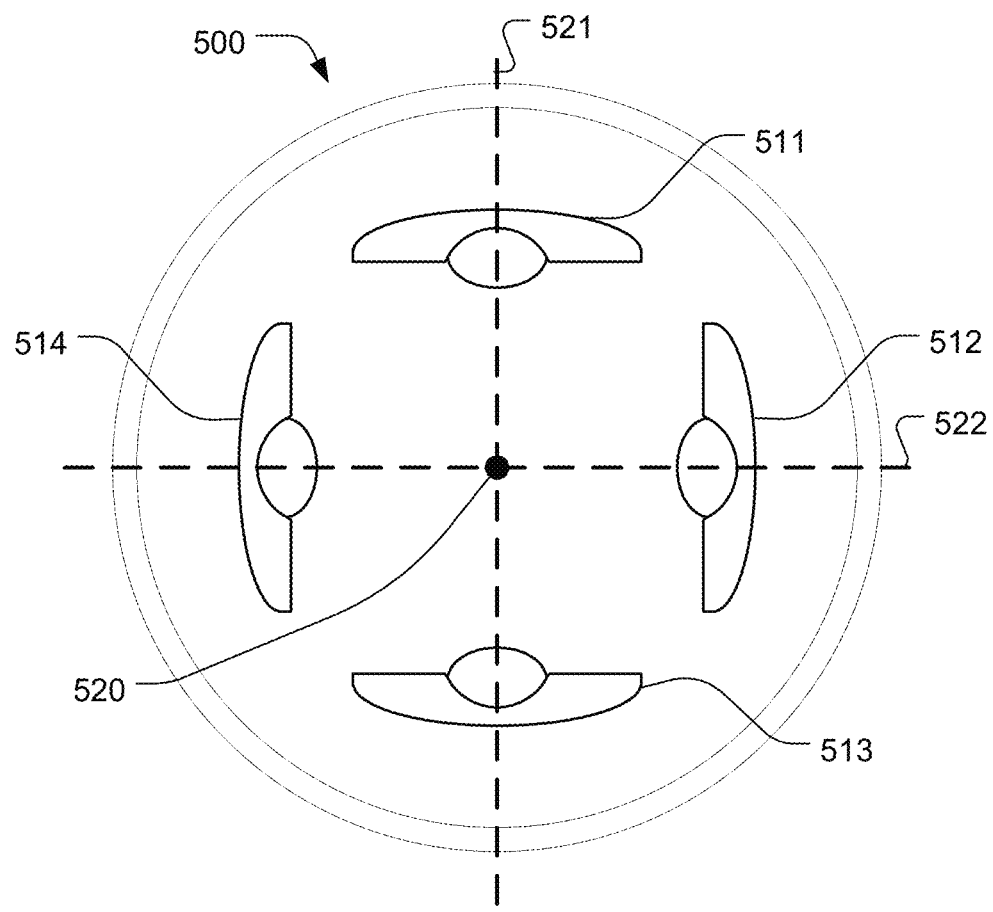
FIG. 5 illustrates a top view of an exemplary lens module with four lens sets to provide combined individual fields-of-view 360°.

There are various types of misalignment between the lens module and the sensor arrays. FIG. 4 illustrates an example of misalignment corresponding to tilting of the of the lens module about the x-axis. The tilting of the lens module may also occur about the y-axis or a combination of the x-axis and y-axis. Furthermore, the center of the lens module and the center of the sensor arrays have to be aligned. FIG. 5 illustrates a top view of the lens module 500, where the partial lens groups (511, 512, 513, 514) are shown. The center of the lens module is indicated by black dot 520. The lens module center 520 has to be aligned with the sensor array center 360. Also, there should be no relative rotation between axes (361, 362) in FIG. 3 and the axes (521, 522) in FIG. 5. The lateral registration between the lens module and the sensor arrays is another degree of freedom to be aligned. While there are up to six degrees of freedom, not all dimensions are available or need for adjustment. For example, a mechanical structure (fixture) may be used to ensure that there is no rotational misalignment between the axes (521, 522) of the lens module and the axes of the sensor arrays (361, 362).

Figure 6:
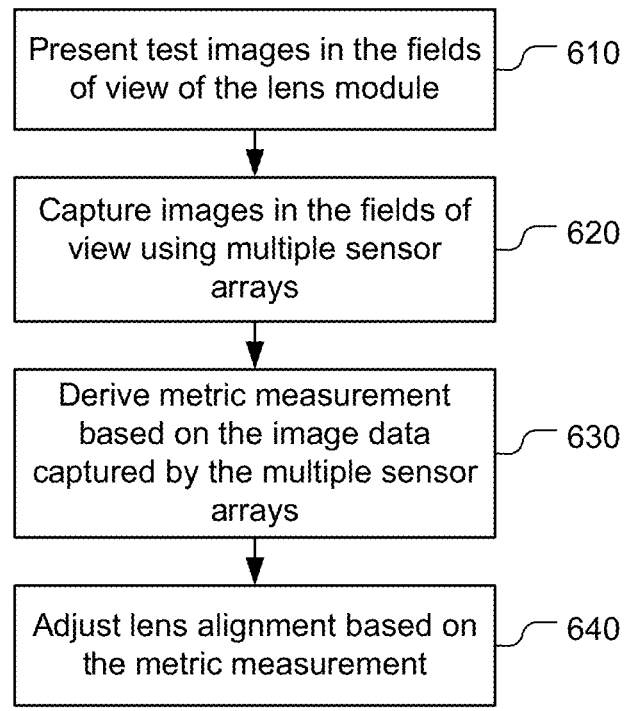
FIG. 6 illustrates an exemplary flowchart for a lens alignment method according to an embodiment of the present invention.

A method of lens alignment according to the present invention utilizes the sensor arrays to capture image signals presented in the fields of view. FIG. 6 illustrates an exemplary flowchart for a system incorporating the lens alignment method according to an embodiment of the present invention. One or more test images are presented in the fields of view of the lens module as shown in step 610. Images in the fields of view are captured using multiple sensor arrays as shown in step 620. Metric measurement is then derived based on the image data captured by the multiple sensor arrays as shown in step 630. Lens alignment is adjusted based on the metric measurement as shown in step 640. The lens alignment process can be applied iteratively until a criterion is met. For example, if the lens adjustment does not further to improve the quality, the lens alignment process can be terminated. Alternatively, using a non-iterative method, a preferred position of the lens module may be calculated from metric measurements derived from one or more test images and the lens module may be moved to the calculated position.

The lens alignment process can be applied to adjust one or more degrees of freedom. After the alignment in the selected one or more degrees of freedom is achieved, the lens alignment process can be applied to one or more other degrees of freedom. The alignment in said one or more other degrees of freedom may affect the alignment achieved in the previous one or more other degrees of freedom. Therefore, iterative lens alignment may be applied between one or more degrees of freedom and one or more other degrees of freedom.

Various test images may be used for the lens alignment according to embodiments of the present invention. For example, one or more "cross hairs", "slant edges", "circles" or "dots" may be used. Other test images, such as "grids", "checker board", "grating lines", and "sinusoidal waves" may also be used.

Figure 7:
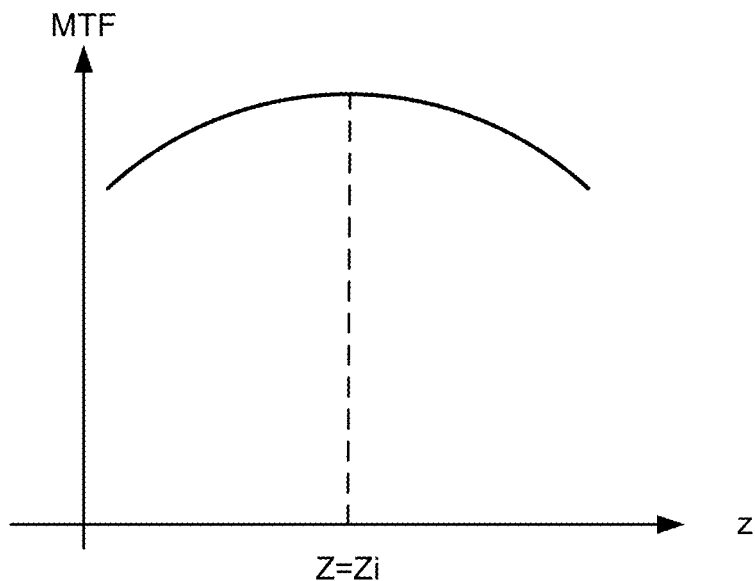
FIG. 7 illustrates an example of metric measurement based on MTF (modulation transfer function).

The metric measurement may correspond to MTF (modulation transfer function), where the optical response to a signal having a selected spatial frequency is measured. Other metric measurement such as point spread function (PSF), spot size of a pin hole, contrast or the maximum achievable spatial resolution. An example of MTF to determine the back focus distance (BFD) of an individual lens set can be used. FIG. 7 illustrates an example of determining the BFD Zi for the i-th sensor array. Zi is the z position which maximizes the MTF. The curve in FIG. 7 may be determined by moving the lens module in the z direction and capturing images at multiple heights, determining the MTF for each image, and interpolation fitting a curve (e.g. spline fit) to the measured MTF data. In practice, determining BFD may use an external camera to image the object plane of a lens set and thus re-image the lens set image plane. The camera takes pictures of the pixel array as the sensor is moved up and down. Best focus for the lens set occurs when the pixels are in focus in the camera. In this case, illumination must be provided back through the lens set to illuminate the sensor.

The measured BFD Zi from four sensor arrays can be used to determine whether the lens is properly aligned with the sensor arrays. For example, motion in Tz, Rx, and Ry directions can be used to minimize focus error. According to one embodiment, Tz, Rx, and Ry can be determined according to:

$$Tz=(Z1+Z2+Z3+Z4)/4, \quad (1)$$

$$Rx=(Z2-Z4)/2d, \text{ and} \quad (2)$$

$$Ry=(Z1-Z3)/2d. \quad (3)$$

The longitudinal distance between the lens module and the sensor arrays in terms of the BFD can be determined according to equation (1), where the distance is determined by averaging the four BFDs measured. On the other hand, the rotational alignment about the x-axis and y-axis can be determined according to equations (2) and (3) respectively, where d is the lateral distance between two corresponding sensor arrays (left and right, or top and bottom). Since d is fixed, only the difference between Z2 and Z4, or Z1 and Z3 will have impact on the measured result. The error for all quadrants after alignment according to the formulas (1)-(3) is:

$$\text{Error}=|Z1-Z2+Z3-Z4|/4. \quad (4)$$

As mentioned previously, the optical center of each the lens set has to be aligned with the center of a corresponding sensor array. The offset between the optical center of the lens set and the center of the sensor array can be represent by (Tx, Ty). In additional, the rotational direction (Rz) of the lens module needs to match with the rotational direction of the sensor arrays. The registration between a lens set in the lens module and the sensor array may be determined by capturing an image with the pixel array where at least a portion of the images edge (the edge of the image footprint) crosses active pixels in the array. Since the shape of the image footprint is known, the registration can be determined even if the entire footprint edge is not imaged. For example, for a lens with circular symmetry, the image footprint is a circle. If the pixel array is smaller than the footprint, a good alignment results in the image footprint edge not appearing in the image at all.

In one embodiment, an illuminated white cylindrical target is used and images of the white cylindrical target captured using individual sensor arrays are used to determine the alignment between an individual lens set and a sensor array. Other target shapes, patterns, and colors may be used as long as the light enters the pupil over the field of view so that at least a portion of the image footprint is visible on the sensor pixel array.

The lens module may be pre-fabricated without capability for adjustment of individual lens set within the lens module after the lens module is pre-fabricated. In this case, while individual translational offset (Txi, Tyi) and rotational error in the z-direction (Rzi) can be measured, an optimal alignment can be achieve according to a desired performance criterion. For example, a least square error can be used as the performance criterion. In another example, a min-max criterion may be used, where the minimum of largest error in (Txi, Tyi) or Rzi is used.

Figure 8:
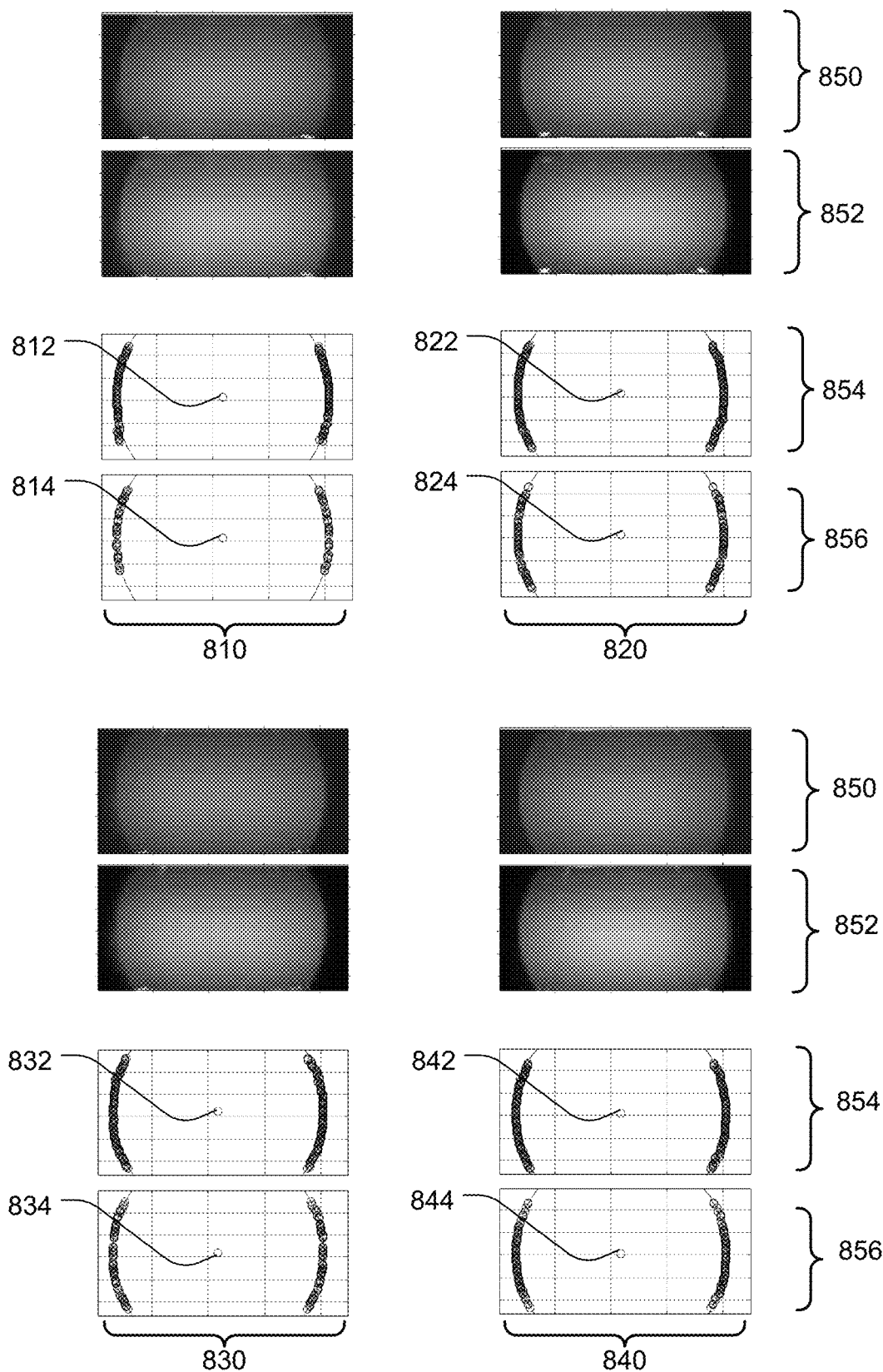
FIG. 8 illustrates an example of using white cylindrical target to find the center of each quadrant and to find the rotation value in the z-direction according to an embodiment of the present invention.

FIG. 8 illustrates an example of using white cylindrical target to find the center of each quadrant and to find the rotation value in the z-direction according to an embodiment of the present invention. The processing is shown for the four lens sets/sensor arrays (810, 820, 830 or 840). The pictures 850 correspond to the original captured image in gray level. Filtering is applied to the captured image to generate smoothed pictures 852. The contours of original pictures and filtered pictures are shown in blocks 853 and 854 respectively. The center of each quadrant is identified as 812, 822, 832 or 842 respectively for the four lens sets based on the original gray image. The center of each quadrant is identified as 814, 824, 834 or 844 respectively for the four lens sets based on the filtered image. The contours are part of the image circle defining the image footprint of each lens set and correspond to the edge of the field of view. Within the image circle, the image is luminous and outside it is dark. The transitional offset (i.e., (Tx, Ty)) and the rotation in the z-direction Rz can be determined based on the extracted contours on the left and right sides.

Figure 9:
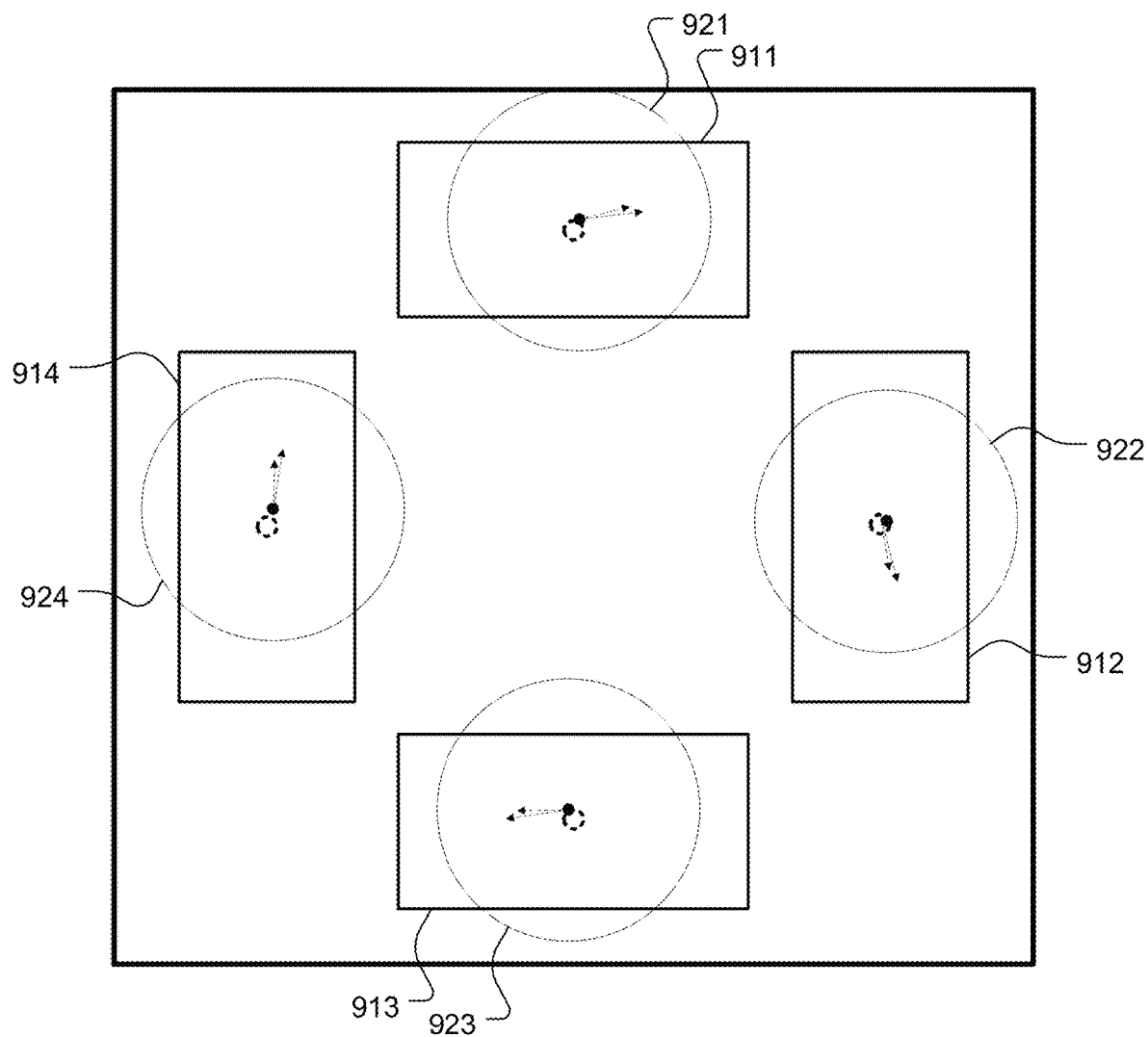
FIG. 9 illustrates an example of transitional offset (i.e., (Tx, Ty)) and the rotation in the z-direction Rz that are determined for four lens sets and sensor arrays.

FIG. 9 illustrates an example of transitional offset (i.e., (Tx, Ty)) and the rotation in the z-direction Rz that are determined for four lens sets and sensor arrays.

The flowchart in FIG. 6 may correspond to software program codes to be executed on a computer, a mobile device, a digital signal processor or a programmable device for the disclosed invention. The program codes may be written in various programming languages such as C++. The flowchart may also correspond to hardware based implementation, where one or more electronic circuits (e.g. ASIC (application specific integrated circuits) and FPGA (field programmable gate array)) or processors (e.g. DSP (digital signal processor)).

In the above disclosure, an example of capsule camera with a lens module consisting of four lens sets is demonstrated. A corresponding sensor chip with four sensor arrays is used. However, any multiple lens sets with a match sensor chip consisting of multiple sensor arrays may be used. For example the lens module may consist of three lens sets and the sensor chip consists of three sensor arrays.

The center of each sensor array is shown as a dashed circle. The circles (921, 922, 923, 924) in FIG. 9 are edges of the image footprints corresponding to the contours in FIG. 8. The center of each edge of the image footprint is indicated by a solid dot. Therefore, the distance between each pair of solid dot and dashed circle corresponds to a respective (Tx, Ty). The rotation in the z-direction, Rz for each lens set and sensor array is indicated by two respective arrows, where one is derived based on the right-side contour and the other is determined based on the left-side contour.

Once the proper alignment is achieved, the position of the lens module can be fixed, e.g. using UV-cured adhesive.

While specific examples are directed to capsule images, the image stitching based on quality of image matching according to the present invention may also be applied to images of natural scenes captured at different viewing angles.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. A method of aligning a lens module with respect to an image sensor device for a capsule camera, wherein the image sensor device comprises multiple pixel arrays and the lens module comprises multiple lens sets to form multiple images corresponding to multiple fields of view associated with the multiple lens sets, and each lens set forms one image for one corresponding pixel array associated with one field of view, the method comprising:

presenting one or more test images in the multiple fields of view associated with the multiple lens sets;

capturing multiple images in the multiple fields of view using the multiple pixel arrays;

deriving metric measurement comprising back focus distances (BFDs) corresponding to substantially parallel optical paths associated with the multiple pixel arrays based on the multiple images captured by the multiple pixel arrays, wherein each back focus distance (BFD) is related to a distance from one image plane of one pixel array to a last lens surface of one corresponding lens set; and adjusting lens alignment between the lens module and the image sensor device based on the metric measurement of the BFDs for the multiple lens sets; and wherein the lens module consists of four lens sets arranged laterally to provide a combined fields-of-view of 360 degrees and the image sensor device consists of four pixel arrays, four BFDs designated as Z1, Z2, Z3 and Z4 associated with four neighboring lens sets are determined, and wherein each of pixel array and one corresponding lens set is used for capturing images in one quadrant; and wherein rotational alignments about x-axis and y-axis are adjusted to minimize (Z2−Z4)/2d and (Z1−Z3)/2d respectively, and wherein d is a lateral distance between two corresponding pixel arrays on two opposite sides and the x-axis and the y-axis are in a plane parallel to the image sensor device.

2. The method of claim 1, wherein the lens alignment between the lens module and the image sensor device is performed in multiple degrees of freedom and second lens alignment in second one or more degrees of freedom is performed after first lens alignment in first one or more degrees of freedom.

3. The method of claim 1, wherein said adjusting the lens alignment between the lens module and the image sensor device is performed in the first one or more degrees of freedom and the second lens alignment iteratively until a criterion is met.

4. The method of claim 3, wherein the criterion corresponds to no further improving image quality by said adjusting the lens alignment.

5. The method of claim 1, wherein said one or more test images are selected from a group comprising "cross hairs", "slant edges", "circles", "dots", "grids", "checker board", "grating lines", and "sinusoidal waves".

6. The method of claim 1, the metric measurement corresponds to modulation transfer function (MTF), point spread function (PSF), spot size of a pin hole, contrast or maximum achievable spatial resolution.

7. The method of claim 1 further comprising fixing adjustable positions of the lens module after adjusting the lens alignment is completed.

8. The method of claim 7, wherein the adjustable positions of the lens module are fixed using UV-cured adhesive.

9. A method of aligning a lens module with respect to an image sensor device for a capsule camera, wherein the image sensor device comprises multiple pixel arrays and the lens module comprises multiple lens sets to form multiple images corresponding to multiple fields of view associated with the multiple lens sets, and each lens set forms one image for one corresponding pixel array associated with one field of view, the method comprising:

presenting one or more test images in the multiple fields of view associated with the multiple lens sets;

capturing multiple images in the multiple fields of view using the multiple pixel arrays;

deriving metric measurement comprising back focus distances (BFDs) corresponding to substantially parallel optical paths associated with the multiple pixel arrays based on the multiple images captured by the multiple pixel arrays, wherein each back focus distance (BFD) is related to a distance from one image plane of one pixel array to a last lens surface of one corresponding lens set; and adjusting lens alignment between the lens module and the image sensor device based on the metric measurement of the BFDs for the multiple lens sets; and wherein the lens module consists of four lens sets arranged laterally to provide a combined fields-of-view of 360 degrees and the image sensor device consists of four pixel arrays, four BFDs designated as Z1, Z2, Z3 and Z4 associated with four neighboring lens sets are determined, and wherein each of pixel array and one corresponding lens set is used for capturing images in one quadrant; and wherein the lens alignment is adjusted to minimize alignment error for all quadrants of the lens module, wherein the alignment error is determined according to |Z1−Z2+Z3−Z4|/4.

10. A method of aligning a lens module with respect to an image sensor device for a capsule camera, wherein the image sensor device comprises multiple pixel arrays and the lens module comprises multiple lens sets to form multiple images corresponding to multiple fields of view associated with the multiple lens sets, and each lens set forms one image for one corresponding pixel array associated with one field of view, the method comprising:

presenting one or more test images in the multiple fields of view associated with the multiple lens sets;

capturing multiple images in the multiple fields of view using the multiple pixel arrays;

deriving metric measurement comprising back focus distances (BFDs) corresponding to substantially parallel optical paths associated with the multiple pixel arrays based on the multiple images captured by the multiple pixel arrays, wherein each back focus distance (BFD) is related to a distance from one image plane of one pixel array to a last lens surface of one corresponding lens set; and adjusting lens alignment between the lens module and the image sensor device based on the metric measurement, wherein said adjusting the lens alignment comprising adjusting translational offset (Tx, Ty) between an optical center of the multiple lens set and a center of the pixel arrays to minimize the translational offset; and wherein the translational offset is determined by using a white cylindrical target as a test image to find a center of each quadrant of the lens module with four lens sets and the center of each quadrant of the lens module is determined from a center of contours of an image of the white cylindrical target.

11. The method of claim 10, wherein the image of the white cylindrical target is filtered prior to finding the center of each quadrant of the lens module.

12. The method of claim 10, wherein said adjusting the lens alignment comprising adjusting rotation value in z-direction, Rz to minimize rotational error, and wherein the z-direction is perpendicular to a plane of the pixel arrays.

13. The method of claim 12, wherein the rotation value is determined contours of the image of the white cylindrical target.

14. The method of claim 12, wherein least square error, a min-max criterion or minimum of largest error in (Tx, Ty) or Rz associated with each quadrant of the lens module is used as a performance criterion.

15. The method of claim 10, wherein a target shape, pattern or color is used as a test image to find a center of each quadrant of the lens module with four lens sets and light associated with test image enters a pupil over a field of view of one lens set so that at least a portion of image footprint of the test image is visible on a corresponding pixel array associated with one field of view.

16. An apparatus for aligning a lens module with respect to an image sensor device for a capsule camera, wherein the image sensor device comprises multiple pixel arrays and the lens module comprises multiple lens sets to form multiple images corresponding to multiple fields of view associated with the multiple lens sets, and each lens set forms one image for one corresponding pixel array associated with one field of view, the apparatus comprising one or more electronic circuits, controllers or processors arranged to:

present one or more test images in the multiple fields of view associated with the multiple lens sets;

capture multiple images in the multiple fields of view using the multiple pixel arrays;

derive metric measurement comprising back focus distances (BFDs) corresponding to substantially parallel optical paths associated with the multiple pixel arrays based on the multiple images captured by the multiple pixel arrays, wherein each back focus distance (BFD) is related to a distance from one image plane of one pixel array to a last lens surface of one corresponding lens set; and adjust lens alignment between the lens module and the image sensor device based on the metric measurement of the BFDs for the multiple lens sets; and wherein the lens module consists of four lens sets arranged laterally to provide a combined fields-of-view of 360 degrees and the image sensor device consists of four pixel arrays, four BFDs designated as Z1, Z2, Z3 and Z4 associated with four neighboring lens sets are determined, and wherein each of pixel array and one corresponding lens set is used for capturing images in one quadrant; and wherein rotational alignments about x-axis and y-axis are adjusted to minimize (Z2−Z4)/2d and (Z1−Z3)/2d respectively, and wherein d is a lateral distance between two corresponding pixel arrays on two opposite sides and the x-axis and the y-axis are in a plane parallel to the image sensor device.

* * * * *